United States Patent [19]

Ryder

[11] Patent Number: 4,750,610

[45] Date of Patent: Jun. 14, 1988

[54] LENS CASE WITH PRESSURE SENSITIVE VENTING SYSTEM

[75] Inventor: Francis E. Ryder, Arab, Ala.

[73] Assignee: Ryder International Corporation, Arab, Ala.

[21] Appl. No.: 946,975

[22] Filed: Dec. 29, 1986

[51] Int. Cl.[4] .......................... B65D 85/38; A61L 2/18
[52] U.S. Cl. ...................................... 206/5.1; 220/208; 220/209; 422/300; 422/310
[58] Field of Search ................ 206/5.1, 438; 220/203, 220/208, 209, 303, 367, 371; 55/385 C; 422/295, 296, 300, 301, 307, 310

[56] References Cited

U.S. PATENT DOCUMENTS

| | | | |
|---|---|---|---|
| 3,173,571 | 3/1965 | Cserny et al. | 220/208 |
| 3,770,113 | 11/1973 | Thomas . | |
| 3,949,934 | 4/1976 | Goglio | 220/208 |
| 4,011,941 | 3/1977 | Parsons . | |
| 4,136,796 | 1/1979 | Dubois et al. . | |
| 4,197,097 | 4/1980 | Magorien et al. . | |
| 4,231,489 | 11/1980 | Malone | 220/367 |
| 4,396,583 | 8/1983 | Le Boeuf . | |
| 4,457,327 | 7/1984 | Pepper | 422/310 |
| 4,469,237 | 9/1984 | Zerdian et al. | 220/209 |
| 4,512,771 | 4/1985 | Norton . | |
| 4,637,919 | 1/1987 | Ryder et al. | 422/300 |

FOREIGN PATENT DOCUMENTS 0223840 3/1958 Australia .............................. 220/367

Primary Examiner—Jimmy G. Foster
Attorney, Agent, or Firm—Trexler, Bushnell, Giangiorgi & Blackstone, Ltd.

[57] ABSTRACT

An appliance for disinfecting contact lenses wherein the lenses are disposed within a disinfecting solution which liberates a gas during the disinfecting process. The appliance has a container body with a removable cap which forms a sealed chamber having a normally closed vent conduit, and a lens holder is provided to support the contact lenses within the container body. The cap includes a resiliently deflectable flange which defines a check valve in the conduit which is deflected by excessive pressure within the container to open the valve enabling passage of effluent gas from the chamber through the conduit.

20 Claims, 1 Drawing Sheet

LENS CASE WITH PRESSURE SENSITIVE VENTING SYSTEM

BACKGROUND OF THE INVENTION

This invention relates to an improved appliance for the chemical sterilization of small articles such as soft contact lenses, and more particularly relates to pressure relief venting of such appliances.

In recent years, extremely soft contact lenses have been fabricated from a pliable plastic material that has the advantage of being able to be worn for extended periods of time without causing discomfort. These plastics are quite hydrophilic, and for that reason these contact lenses are susceptible to contamination by microorganisms. Consequently, the user must sterilize or disinfect the lenses, generally on a daily basis.

Various disinfecting techniques are now used in which the lenses are heated in a closed vessel in the presence of a saline solution, the heat being of such intensity and duration as to destroy the contaminating microorganism. More recently, a sterilizing process has been utilized that does not require heating. This process utilizes a bactericide, for example hydrogen peroxide, which oxidizes the bacteria on the lenses. In accordance with this process, the lenses are immersed for several hours in a weak solution of hydrogen peroxide, generally a 3% solution. Also within the solution is a platinum catalyst which hastens the decomposition of the hydrogen peroxide. If a bactericide such as hydrogen peroxide is used, care must be taken to insure that the solution is sufficiently neutralized or broken down so that the possibility of discomfort or injury to the eye of the user is precluded. Accordingly, the lenses are kept in the bactericide solution for a sufficient length of time to destroy all of the bacteria, following which the lenses are introduced into a rinsing solution to rinse out excess bactericide which may have a concentration that is unacceptably high.

Another problem encountered in the foregoing process is that there is a buildup of gas pressure within the sterilizing chamber which may tend to cause leaking and/or spillage, especially when the cap of the unit is not sealed properly. In this regard, when the hydrogen peroxide is brought into contact with the platinum catalyst, the hydrogen peroxide solution tends to break down into water, with oxygen being liberated. The liberated oxygen will cause a pressure build-up within the vessel that must be vented to the atmosphere. In U.S. Pat. No. 4,011,941, there is shown and described a contact lens sterilizer using hydrogen peroxide and in which the oxygen pressure is relieved through the expansion of a rubber O-ring. Thus, the O-ring normally seals the unit, but also functions as a check valve. However, when the valve is "open", there is still the possibility of solution leaking therethrough. Moreover, an O-ring can lose its resiliency over a period of time causing improper or ineffective valve operation. Additionally, the O-ring can become displaced leaving an opening through which bacteria from the ambience may enter the sterilizing chamber.

In U.S. patent application Ser. No. 668,293, filed Nov. 5, 1984 (now allowed), which is incorporated herein by reference, an appliance is described for disinfecting contact lenses or the like which employs a hydrophobic membrane filter that continuously vents the buildup of gas within the unit during the disinfecting process, while at the same time keeping the unit effectively sealed against leakage of disinfecting solution and entrance of bacteria into the sterilizing chamber.

OBJECTS AND SUMMARY OF THE INVENTION

An object of the invention is to provide an appliance for disinfecting contact lenses in which pressure relief venting of gas generated in the disinfecting process is not limited by the rate of the gas permeation through a filter membrane.

A further object of this invention is to provide an appliance of the type stated in which the disinfecting process can be carried out until the bactericide has been completely reduced which, in the case of hydrogen peroxide, results in liberation of sufficient oxygen to reduce the hydrogen peroxide to water.

In accordance with the foregoing objects, the invention comprises an appliance for disinfecting contact lenses or the like wherein the lenses are disposed within a disinfecting solution which liberates a gas during the disinfecting action, said appliance comprising a container having a container body including an opening at one end thereof, a removable cap for closing said opening to form with said body a sealed chamber having a normally closed vent conduit therefrom; lens holder means for supporting contact lenses within said container body; said cap including a resiliently deflectable flange means defining a check valve in said conduit for deflection by excessive pressure within said container to open said valve enabling passage of effluent gas from said chamber through said conduit.

In another aspect of the invention, the cap and the opening end of the container body are threaded together to provide a clearance space between the respective threads which forms a portion of the vent conduit for effluent gas from the opened check valve.

In another aspect of the invention, the appliance includes a vent passageway from the chamber and a gas permeable filter medium, preferably a membrane, is disposed across the passageway for venting only the liberated gas through the filter medium.

DETAILED DESCRIPTION

Figure 1:
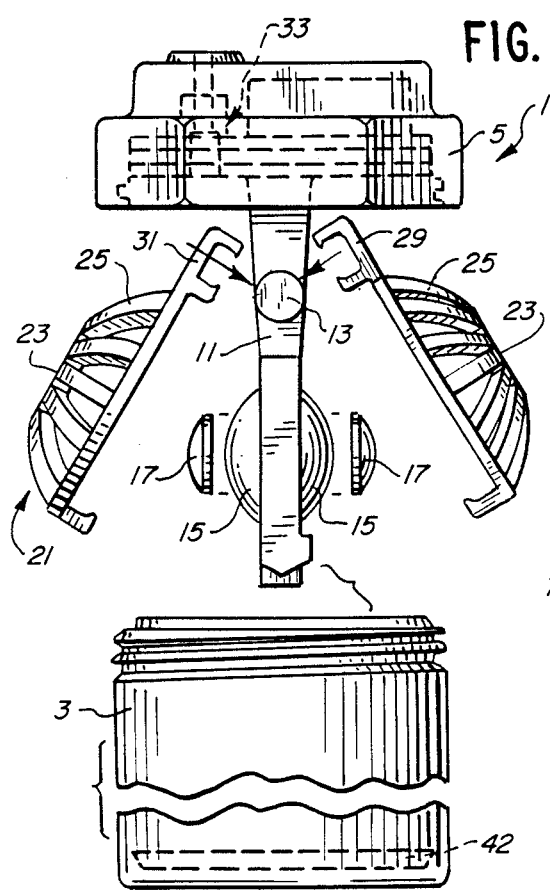
FIG. 1 is an exploded partial elevational view of a lens disinfecting appliance in one embodiment of the invention.
Figure 4:
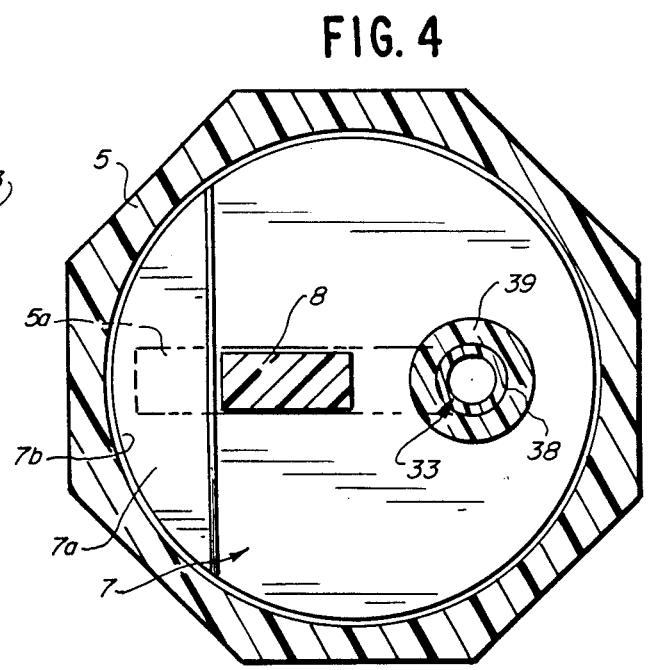
FIG. 4 is a sectional view taken along line 4—4 in FIG. 2 and viewed in the indicated direction.
Figure 2:
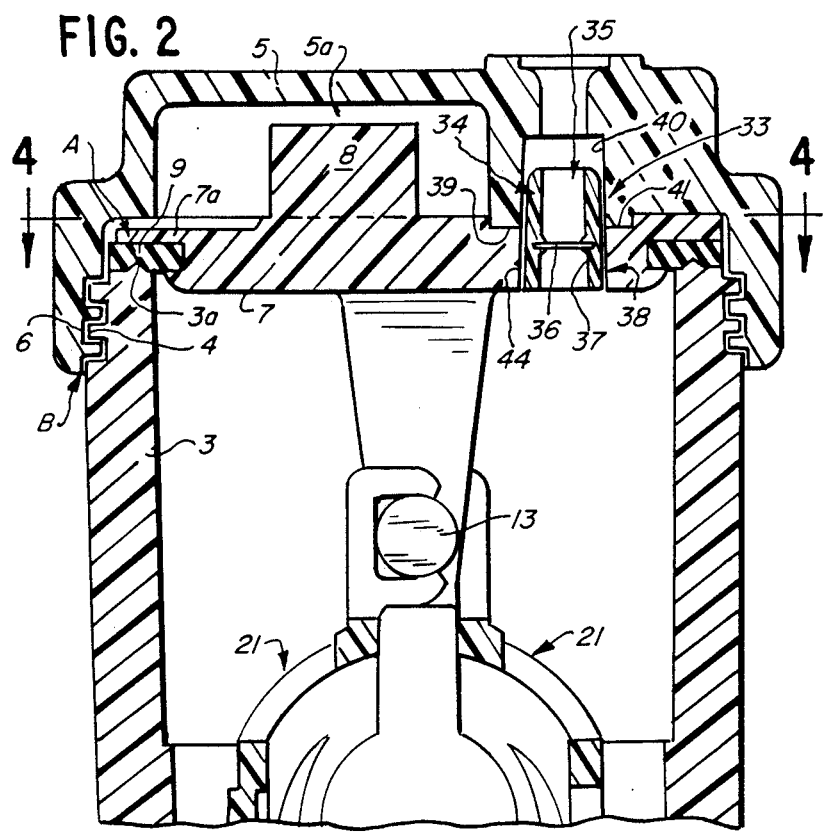
FIG. 2 is an enlarged, partial sectional view of the assembled container cap and body shown in FIG. 1.

Referring now in more detail and by reference characters to the drawings, which illustrate a preferred embodiment of the present invention, there is shown a lens case 1 comprising a container 3 with a generally cylindrical body having an end opening around which are formed threads for receiving a removable screw cap 5. The container 3 and the screw cap 5 are each molded from suitable plastic material. Mounted in the screw cap 5 is a disc 7, the grooved periphery of which seats an annular gasket 9 which seals against the end rim 3a of the container 3 at its opening. As best shown in FIGS. 2 and 4, the disc 7 has an upstanding tongue 8 which fits into an aligning mortise 5a formed in the cap 5.

Referring to FIG. 2, a pressure relief check valve is generally designated by reference character A. As shown particularly in FIGS. 2 and 4, the circular disc 7 includes a flange portion 7a which extends to and is partially defined by a portion of the peripheral edge 7b which overlies and engages the gasket 9. In the upper plan view of the disc 7 in FIG. 4, the planar configuration of the flange 7a generally conforms to a geometric section of the circular disc 7 in the illustrated embodiment of the lens case 1; the flange 7a can have a different, suitably resilient configuration so long as it extends to the peripheral edge 7b. As best shown in FIG. 2, the flange 7a is reduced in thickness relative to the main body of the disc 7 with which the flange 7a is integrally molded. The reduced thickness enables the flange 7a to resiliently deflect relative to the main body of the disc 7; excessively high pressure generated within the container 3, as more fully described hereinafter, will force the gasket 9 and flange 7a to deflect upwardly away from the end rim 3a of the container wall 3, which together with the gasket 9 and flange 7a form the relief vent check valve generally designated by reference character A.

The radially exterior surface of the container adjacent the end 3a is threaded so that the threading 4 and the threading 6 on the interior of the cap 5 are separated by a clearance space B and have a generally loose fit. When the excessive pressure within the container 3 forces upward deflection of the gasket 9 and flange 7a away from the wall end 3a to open the check valve A, the excessive pressure will be relieved by passage of gas from the interior of a container between the gasket 9 and end 3a of the opened check valve A and therefrom the gas passes through the clearance space B formed by the loose fit between the threads 4 and 6 from which the effluent gas passes to the ambience of the appliance 1; the flow path of the effluent gas is indicated by the arrows in FIG. 3. When the pressure has been relieved by passage of sufficient effluent gas to reduce the pressure within the container 3 to an acceptable level, for example, below approximately 40 psig., the gasket 9 and flange 7a will resiliently deflect downwardly and return to the normal positions indicated by FIG. 2 in which the gasket 9 is again sealed against the end rim 3a.

Figure 5:
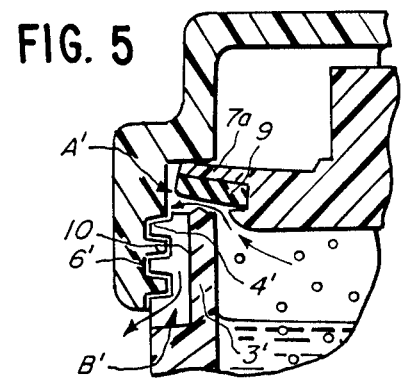
FIG. 5 is a sectional view similar to FIG. 3, illustrating a modified embodiment of the invention in which a slot is provided in the container body for passage of gas from the opened check valve.

Referring to the modified embodiment in FIG. 5, the container wall 3' can be fabricated to include a generally vertically oriented slot 10 which is aligned below the flange 7a when the cap 5 is sufficiently threaded onto the container 3 for the gasket 9 to seal the rim 3a; the slot 10 interrupts the threading 4' and enlarges the clearance B' between the threading 6' and the container wall 3' to enable increased effluent flow rate of the gas when the check valve A' has been opened by excessive pressure within the container. The slot 10' also provides clearance for passage of the effluent gas regardless of how tightly the threads 4' and 6' are engaged, particularly when no thread clearance is provided at all (not shown). Optionally, the slot can be provided through the threading of the cap.

The upper disc 7 forms part of a depending lens-supporting frame 11 which is integrally molded with the disc 7 and projects downwardly into the container 3 when the cap 5 is mounted thereon. Integrally molded on the frame 11 are opposed, axially aligned trunions or pins 13, 13, and below the pins 13, 13, is a button-like structure having opposed convex lens-receiving surfaces 15, 15. These surfaces 15, 15 receive the concave sides of the plastic contact lenses 17, 17. The button-like structure forming the convex lens-receiving surfaces 15, 15 is suspended from the remainder of the depending frame 11 by a series of ribs 19, permitting the passage of fluid through the frame 11.

Mounted on the pins 13, 13 are opposed lens covers 21, 21. Each lens cover has an end piece 23, 23 and a series of spokes 25, 25 radiating therefrom and being joined to respective rims 27, 27. At its upper end, each cover has a pair of fingers 29, 31 which snap-fit over the pins 13, 13 when the covers 21 are mounted onto the pins 13, 13. When so mounted, each cover swings independently of the other cover about the axis of the pins 13, 13. When in the fully-closed position, the covers 21, 21 retain the lenses 17, 17 on the lens supporting surfaces 15, 15.

Affixed in the preferred embodiment of the cap 5 is a hydrophobic membrane filter assembly 33 shown in FIGS. 2 and 4 which enables normal venting of generated oxygen when the pressure within the container is not high enough to require relief through the check valve A, permeable to gaseous oxygen but not to hydrogen peroxide solution. The membrane also prevents bacteria and other contaminants from entering the lens case 1. This filter assembly 33 comprises a tapered tubular member 34 having a bore 35. The bore 35 may have a larger diameter portion 37 at the larger diameter end of the tube 34. A filter medium 36 is carried by the tube 34 and is clinched throughout its entire periphery by the plastic of the tube 34 to provide a liquid-tight barrier across the bore of the tube. The filter medium is a membrane filter having pores which are sized at approximately 0.2 microns. The preferred filter medium is an acrylic copolymer cast on a nylon non-woven substrate. The material is available commercially from Millipore Corporation, Concord, Mass. The member 34 is molded as an individual piece with the filter medium therein prior to assembly with the cap 5.

In assembly of the appliance, the upper disc 7 with attached depending frame 11 is fabricated separately from the cap 5. The cap 5 is provided with a bore 40 surrounded by a boss 41, which bore 40 is slightly tapered. As best seen in FIG. 2, the upper disc 7 is formed with a bore 38 having a counterbore 39 to accommodate the boss 41. Upon assembly, the disc 7 is initially disposed within the cap 5, and the bore 38 is placed in alignment with bore 40 in the cap proper. The boss 41 and counterbore 39 cooperate to facilitate proper initial alignment. Thereafter, the periphery of the disc 7 is ultrasonically welded to the cap. After welding, the filter assembly 33 is pressed into the aligned holes 38, 40 such that the bore of the tubular filter support forms part of the vent and with the opening across the vent being obstructed only by the filter medium 36. The respective tapers on the tubular member 34 and bore 40 serve to provide a wedge type seal that prevents the entry of contaminants. Also it should be noted that end of the bore 38 opposite the counterbore 39 has a reduced diameter portion 44 of an inner diameter less than the outer diameter of the larger diameter end of the tube member 34. Thus, upon insertion of the filter assembly 33, the larger diameter end of member 34 will be received within the bore 38 with a snap-type fit, the larger diameter end of member 34 snapping past the reduced diameter end portion 44 to effect a positive retention of the filter assembly 33 within the aligned bores 40 and 38.

Insertion of the filter assembly 33 after welding of the disc 7 to the cap 5 is an important feature. Should the filter assembly be assembled prior to the ultrasonic welding of the disc 7 and cap 5, there is a danger that the ultrasonic waves will damage, if not destroy, the hydrophobic membrane 36.

In use, the soft contact lenses 17 are placed within the lens support and are held in place by the covers 21. Hydrogen peroxide sterilizing solution is then poured into the open end of the container 3, and in addition, a catalyst 42 may then be introduced into the solution. Alternatively, the catalyst, which is disclosed in said earlier mentioned U.S. Pat. No. 4,011,941 may be disposed within container 3 prior to introduction of the sterilizing solution. This catalyst comprises a catalytic reactor member with the preferred catalytic material being a very thin layer of platinum black which has been deposited on a molded substrate of the desired shape. As the reaction proceeds, the oxygen liberated upon decomposition of the hydrogen peroxide will be vented through 0.2 micron pores of membrane 36, but the liquid will not leak therethrough. This membrane also will prevent any bacteria or contaminants from entering the lens case 1.

Figure 3:
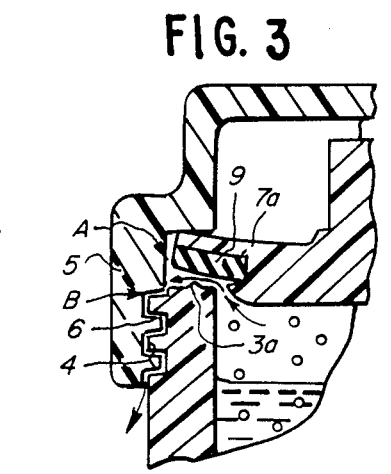
FIG. 3 is a sectional view broken away from FIG. 2 illustrating passage of gas through an opened check valve formed by the container cap and body.

However, if oxygen is generated at a rate much greater than the rate at which the oxygen can be passed through the membrane 36 or if membrane 36 becomes clogged or otherwise ceases to function, so that a resulting excessively high pressure is produced within the container 3, the pressure exerted on the gasket 9 will cause resilient deflection of the flange 7a to open the check valve A enabling the pressure relief action described with reference to FIGS. 3 and 5. Thus, the pressure relief provided by the venting of gas through the opened check valve A eliminates the possibility of stress cracking in the container 3 as well as eliminating the risk of explosion caused by generation of excessive pressure within the container, particularly in the event of accidental blockage of the membrane 36 which would fail to provide the normal venting of effluent oxygen.

Optionally, the flange 7a can be fabricated and dimensioned to provide the primary venting of effluent gas during the disinfecting process so that the filter assembly and venting membrane can be entirely eliminated from the lens case. In such a modified lens case, the thickness and configuration of the flange can be fabricated so that the flange will resiliently deflect to open the check valve when the pressure within the case exceeds, for example, approximately 25 psig. and after venting gas to reduce the pressure, the flange will reverse its deflection to close the valve. Repeated opening and closing of the valve by deflections of the flange will provide the primary venting of the gas throughout the disinfection process so that there is no risk of plugging a filter membrane or entry of microbiological contamination through such a membrane.

While a preferred embodiment of the present invention is illustrated and described, it is envisioned that those skilled in the art may devise various modifications once possessed of this disclosure. Accordingly, the invention is to be defined by the spirit and scope of the claims appended hereto, and is not limited to the specific embodiment disclosed.

The invention is claimed as follows:

1. An appliance for disinfecting contact lenses or the like wherein the lenses are disposed within a disinfecting solution which liberates a gas during the disinfecting action, said appliance comprising a container having a container body including an opening at one end thereof, a removable cap for closing said opening to form with said body a sealed chamber having a normally closed vent conduit therefrom; lens holder means for supporting contact lenses within said container body; said cap including a resiliently deflectable flange means defining a check valve in said conduit for deflection by excessive pressure within said container to open said valve enabling passage of effluent gas from said chamber through said conduit, wherein said cap and said opening end of said container body are loosely threaded to provide clearance space between respective threads thereon, and wherein said clearance space defines a portion of said conduit for enabling passage of effluent gas from said open check valve when said cap and container body are fully threaded together.

2. The appliance according to claim 1 wherein said check valve is further defined by a normal seal between said flange means and said opening end of the container body, in the closed position of said valve.

3. The appliance according to claim 2 further comprising gasket means mounted against said flange means and deflectable therewith, said gasket means normally engaging said opening end of the container body to provide said seal.

4. The appliance according to claim 2 wherein said cap comprises a closure disc on which gasket means is carried for normally sealing engagement with said opening end of the container body.

5. The appliance according to claim 4 wherein said flange means is mounted on said disc.

6. The appliance according to claim 4 wherein said flange means is integral with said disc.

7. An appliance for disinfecting contact lenses or the like wherein the lenses are disposed within a disinfecting solution which liberates a gas during the disinfecting action, said appliance comprising a container having a container body including an opening at one end thereof, a removable cap for closing said opening to form with said body a sealed chamber having a normally closed vent conduit therefrom; lens holder means for supporting contact lenses within said container body; said cap including a resiliently deflectable flange means comprising gasket means sealing against said opening end of said container body and defining a normally closed check valve in said conduit for deflection by excessive pressure within said container to open said valve enabling passage of effluent gas from said chamber through said conduit, wherein said flange means comprises an integral portion of a closure disc having a reduced thickness enabling resilient deflection of said flange portion relative to said disc.

8. The appliance of claim 7 wherein said flange portion extends to and is partially defined by a peripheral edge of said disc.

9. The appliance according to claim 8 wherein said disc has a generally circular configuration and said flange portion is defined by a geometric section of said disc.

10. An appliance for disinfecting contact lenses or the like wherein the lenses are disposed within a disinfecting solution which liberates a gas during the disinfecting action, said appliance comprising a container having a container body including an opening at one end thereof, a removable cap for closing said opening to form with said body a sealed chamber having a normally closed vent conduit therefrom; lens holder means for supporting contact lenses within said container body; said cap including a resiliently deflectable flange means defining a check valve in said conduit for deflection by excessive pressure within said container to open said valve enabling passage of effluent gas from said chamber through said conduit, wherein said cap and container body are threaded together to close said opening, and wherein said threading is interrupted by a slot formed in one of said cap and container body, said slot forming a portion of said conduit for passage of effluent gas from said opened check valve.

11. An appliance for disinfecting contact lenses or the like wherein said lenses are disposed within a disinfecting solution which liberates a gas during the disinfecting action, said appliance comprising a container having a container body including an opening at one end thereof; a removable cap for closing said opening to form with said body a sealed chamber having a normally closed vent conduit therefrom; lens holder means for supporting contact lenses within said container body; said cap including a resiliently deflectable flange means defining a check valve in said conduit for deflection by excessive pressure within said container to open said valve enabling passage of effluent gas from said chamber through said conduit; and a vent passageway from said chamber, including a gas permeable filter medium disposed across said passageway for venting only said liberated gas through said medium wherein said medium is mounted within the bore of a tubular filter support defining said passageway and wherein said tubular filter support is mounted within a bore formed through said cap.

12. The appliance according to claim 11 wherein said medium comprises a membrane including pores having approximately 0.2 micron effective diameter.

13. The appliance according to claim 11 wherein said check valve is further defined by a normal seal between said flange means and said opening end of the container body, in the closed position of said valve.

14. The appliance according to claim 11 further comprising gasket means mounted against said flange means and deflectable therewith, said gasket means normally engaging said opening end of the container body to provide said seal.

15. The appliance according to claim 14 wherein said flange means comprises a portion of said disc having a reduced thickness enabling resilient deflection of said flange portion relative to said disc.

16. The appliance of claim 14 wherein said flange portion extends to and is partially defined by a peripheral edge of said disc.

17. The appliance according to claim 16 wherein said disc has a generally circular configuration and said flange portion is defined by a geometric section of said disc.

18. The appliance according to claim 11 wherein said cap comprises a closure disc on which gasket means is carried for normally sealing engagement with said opening end of the container body.

19. The appliance according to claim 11 wherein said cap and said opening end of said container body are loosely threaded to provide clearance space between respective threads thereon, and wherein said clearance space defines a portion of said conduit for enabling passage of effluent gas from said open check valve when said cap and container body are fully threaded together.

20. The appliance according to claim 11 wherein said cap and container body are threaded together to close said opening, and wherein said threading is interrupted by a slot formed in one of said cap and container body, said slot forming a portion of said conduit for passage of effluent gas from said open check valve.

* * * * *